(12) United States Patent
Becker

(10) Patent No.: US 9,700,706 B2
(45) Date of Patent: *Jul. 11, 2017

(54) NASOLACRIMAL OBSTRUCTION TREATMENT DEVICE AND METHOD

(71) Applicant: Bruce B. Becker, Malibu, CA (US)

(72) Inventor: Bruce B. Becker, Malibu, CA (US)

( * ) Notice: Subject to any disclaimer, the term of this patent is extended or adjusted under 35 U.S.C. 154(b) by 179 days.

This patent is subject to a terminal disclaimer.

(21) Appl. No.: 14/520,052

(22) Filed: Oct. 21, 2014

(65) Prior Publication Data

US 2015/0039013 A1 Feb. 5, 2015

Related U.S. Application Data

(63) Continuation of application No. 12/831,133, filed on Jul. 6, 2010, now Pat. No. 8,864,746, which is a continuation of application No. 11/441,558, filed on May 26, 2006, now abandoned.

(51) Int. Cl.
| | | |
|---|---|---|
| *A61M 29/02* | (2006.01) | |
| *A61M 25/10* | (2013.01) | |
| *A61M 29/00* | (2006.01) | |
| *A61M 25/00* | (2006.01) | |
| *A61F 9/007* | (2006.01) | |

(52) U.S. Cl.
CPC ......... *A61M 29/02* (2013.01); *A61F 9/00772* (2013.01); *A61F 9/007* (2013.01); *A61M 25/10* (2013.01); *A61M 29/00* (2013.01); *A61M 2025/0042* (2013.01); *A61M 2025/1054* (2013.01)

(58) Field of Classification Search
CPC .......... A61M 29/02; A61M 2210/0606; A61M 2210/0612; A61M 2210/0618; A61M 2025/1054; A61F 9/00772; A61F 2250/0003; A61F 2/186
See application file for complete search history.

(56) References Cited

U.S. PATENT DOCUMENTS

| | | | | |
|---|---|---|---|---|
| 4,137,922 A | * | 2/1979 | Leininger | A61M 29/02 604/913 |
| 4,441,495 A | * | 4/1984 | Hicswa | A61B 17/12109 604/103 |
| 4,517,979 A | * | 5/1985 | Pecenka | A61B 17/12109 604/907 |
| 4,545,367 A | * | 10/1985 | Tucci | A61B 17/12109 128/898 |
| 5,029,574 A | * | 7/1991 | Shimamura | A61B 1/00082 600/108 |

(Continued)

*Primary Examiner* — Adam Marcetich
(74) *Attorney, Agent, or Firm* — Charmasson, Buchaca & Leach, LLP

(57) ABSTRACT

A device and method for performing probing and intubation of the nasolacrimal system includes a tubular probe through which a tracer fluid is injected and collected in the nasal cavity to verify that the tip of the probe has passed through an obstruction and reached the nasal cavity. A sleeve fitted over the probe has distal segment that is inflated in order to retain the sleeve in the nasolacrimal system once the tubular probe has been withdrawn. Removal of blood and other obstructions encountered during the probing or intubation process is accomplished by connecting the proximal end of the probe to a suction device.

15 Claims, 4 Drawing Sheets

(56) References Cited

U.S. PATENT DOCUMENTS

| | | | | |
|---|---|---|---|---|
| 5,423,777 | A * | 6/1995 | Tajiri | A61B 17/12022 604/294 |
| 8,864,746 | B2 * | 10/2014 | Becker | A61M 29/02 604/317 |
| 2004/0068286 | A1 * | 4/2004 | Mendius | A61B 17/12099 606/191 |
| 2006/0271092 | A1 * | 11/2006 | Reed | A61M 29/02 606/193 |
| 2006/0276738 | A1 * | 12/2006 | Becker | A61F 9/00772 604/8 |
| 2007/0083146 | A1 * | 4/2007 | Murray | A61F 9/00772 604/8 |

\* cited by examiner

NASOLACRIMAL OBSTRUCTION TREATMENT DEVICE AND METHOD

PRIOR APPLICATION

This is a continuation of U.S. patent application Ser. No. 12/831,133, filed Jul. 6, 2010, now U.S. Pat. No. 8,864,746, issued Oct. 21, 2014 which is a continuation of U.S. patent application Ser. No. 11/441,558, filed May 26, 2006 abandoned.

FIELD OF THE INVENTION

The present invention relates to devices used for normalizing the flow of fluid in tubular organs of human bodies that have been injured by a disease or an accident. More specifically, the invention relates to probes and stents used in treating canalicular and nasolacrimal duct stenosis, obstruction, lacerations or other trauma.

BACKGROUND

The orbital portion of the lacrimal gland is located in the superotemporal orbit and the palpebral portion of the lacrimal gland is located on the posterior surface of the superotemporal upper lid. The lacrimal gland produces the aqueous portion of the tear film. Ductules from the orbital portion of the lacrimal gland pass through the adjacent palpebral lacrimal gland to empty in the superior conjunctival cul-de-sac. Smaller accessory lacrimal glands in the upper and lower lids also contribute to tear production. The tears bathe the surface of the eye and then drain into the puncta and canaliculi in the medial upper and lower lids. The superior and inferior canaliculi join as the short common canaliculus. The tears flow from the superior and inferior canaliculi through the common canaliculus, into the lacrimal sac, and down the nasal lacrimal duct into the nose.

The canaliculi can become obstructed or stenotic on a congenital basis or from trauma such as lacerations, from inflammation, from certain types of chemotherapy, such as taxotere or five-fluorouracil—which may also affect the nasolacrimal duct—or the obstruction can be idiopathic. When the upper and lower canaliculi or the common canaliculus become obstructed, tears can no longer drain from the surface of the eye through the lacrimal system into the nose. The tears well up in the eye as a result, and run down the face. The excess tears blur the vision and the patient has to constantly dab the eye.

The nasolacrimal duct can also become obstructed and, as a result, damaged as a result of a congenital obstruction or an acquired obstruction. Tears stagnating in the lacrimal sac and bacteria multiplying therein lead to an infection of the lacrimal sac in many patients suffering from nasolacrimal duct obstruction. The result is a painful enlargement of the lacrimal sac swollen with pus, and a discharge over the eye.

Canalicular obstruction or stenosis is usually treated by forming a new passage through the obstruction with a probe, also by dilatation with probes or with a balloon catheter. At times, a dacryocystorhinostomy (DCR) is performed. A DCR consists of the surgical creation of a new passageway from the lacrimal sac into the nasal cavity. This can be performed with a balloon catheter using an endoscope or externally through an incision. A silicon tube is most often placed in the lacrimal system whether or not a DCR is performed.

In the case of trauma to the lacrimal drainage system, an intubation is performed to prevent scars from permanently clogging the canaliculi or nasolacrimal duct. In cases of canalicular or nasolacrimal duct obstruction from chemotherapy, intubation is performed as quickly as possible to prevent complete, irreversible closure.

Congenital nasolacrimal duct obstruction is treated with probing or through balloon catheter dilatation. However, intubation is also needed in some resistant cases.

Accordingly, intubation of the lacrimal system preferably with a silicon tube, is often performed after lacrimal surgery or as a primary treatment for nasolacrimal duct obstruction, canalicular stenosis, or canalicular laceration. The easiest device to insert is the Mini-monoka tube that consists of a silicon tube attached to a punctal plug. The tube is inserted through one canaliculus into the lacrimal sac. The plug on the proximal end of the tube is positioned at the punctum. The tube will thus stay in place without having to enter the nasolacrimal duct or the nose. Indeed, the Mini-monoka tube cannot generally be placed in the nasolacrimal duct or nose. If, however, intubation of the nasolacrimal duct is needed, then one of the two ends of the silicon tube is threaded through the canaliculus and down the nasolacrimal duct into the nose. The distal end of the tube, or of any probe attached to it, must be grasped in the nose and pulled into position. It can be very difficult to locate and grasp the tube in the nose of some patients. In some cases, it is impossible to find the tube. That is because the nasolacrimal duct empties into the nasal cavity in the inferior meatus beneath the inferior turbinate. U.S. Pat. No. 6,383,192 discloses a way to push an intubation device by means of a rod. However this method still require pulling the device out of the lacrimal duct from inside the nasal cavity. The nasolacrimal duct is very hard or impossible to visualize even with the help of a flexible endoscope. It is also very difficult to locate the duct simply by tactile sensation with an instrument. U.S. Pat. No. 6,878,165 Makino teaches another verification method involving the insertion of a miniature light at the tip of a probe or stent. The illumination of the nasal cavity offers visual proof that penetration is complete, unless, as is usually the case, the light is blocked by an edema or an accumulation of blood.

Obstruction of the nasolacrimal duct occurs in 2 percent to 6 percent of newborns. Congenital nasolacrimal duct obstruction usually resolves with the use of antibiotic drops and massage of the lacrimal sac. However, a significant number of patients require surgical treatment for congenital nasolacrimal duct obstruction. A probing is usually performed in these children. If silicone intubation needs to be performed, then the location and course of the nasolacrimal duct may need to be confirmed by probing before performing intubation of the lacrimal system.

Probing is performed by inserting a probe horizontally through the punctum and canaliculus into the lacrimal sac. The probe is then oriented vertically and pushed down the nasolacrimal duct into the nasal cavity. The surgeon must then confirm that the probe has penetrated all obstructions in the nasolacrimal duct and reached the nasal cavity. This is commonly done by placing a metal instrument into the nose and touching the probe. The surgeon feels for metal on metal contact indicating that the probe has entered the nasal cavity.

The probe is then removed from the lacrimal system. A syringe filled with fluorescein stained water with an attached short cannula is placed in the canaliculus and the fluid is irrigated through the lacrimal system into the nose. The fluid is recovered in the nose with a suction catheter. This confirms that the lacrimal system is patent after the probing. If the fluid does not irrigate into the nose, then the probing is repeated.

Probing presents several problems. The probe enters the nasal cavity through the opening of the nasolacrimal duct in the lateral nasal wall beneath the inferior turbinate. This area is difficult to access, making it often impossible for the surgeon to touch the probe in the nose with another instrument. In this event, the surgeon cannot confirm if the probe has entered the nasal cavity. Another problem is that irrigation of the lacrimal system is required to determine if the nasolacrimal duct obstructions have been opened. If irrigation through the lacrimal system down to the nasal cavity is not verified, the probing must be repeated. As a result, multiple procedures are performed that can cause repeated trauma to the lacrimal drainage system with each placement of a probe or cannula.

Bleeding in the lacrimal system or nose often occurs during the probing, intubation or associated procedures. The applicant is not aware of any expedient and practical device for clearing blood from the lacrimal system. Furthermore, the only known method for removing blood from the nasal cavity is by introducing into the nose a suction catheter through the naris. It is often difficult if not impossible to position the catheter in the inferior meatus in order to remove blood around the nose end entry into the nasolacrimal duct.

The probes of the prior art are solid metal rods made of steel, bronze, silver or other metal. A flattened area in the center of the probe facilitates its manipulation.

The instant invention results from attempts to achieve intubation without having to retrieve the end of the tube inside the nose, to perform probing and irrigation in a single step, to expediously clear blood and other fluids from the nasal cavity and the nasolacrimal duct.

SUMMARY

The instant embodiments provide a simple and practical method for verifying that a nasolacrimal system probe or intubation sleeve has been inserted through all obstructions down to the nasal cavity. In some embodiments the new probe comprises a tube shaped and dimensioned to penetrate a patient's canaliculus and nasolacrimal duct. In some embodiments the tube has an axial lumen through which a tracing fluid can be injected. In some embodiments recovery of the fluid in the nasal cavity indicates that the probe has passed through any obstructions in any part of the system.

Some embodiments offer a novel method of intubation of the nasolacrimal system using a sleeve that fits over the aforesaid probe and can be threaded all the way down the nasal cavity through a patient's punctum, canaliculus, lacrimal sac and nasolacrimal duct. The tip of the sleeve can be inflated to stabilize its position before the probe is withdrawn. The probe can be used to irrigate the nasolacrimal system with a tracing fluid which once recovered through a suction apparatus in the nasal cavity provides a positive indication that the sleeve is in place.

A version of the probe can be adapted to suction blood, and other fluids from the nasolacrimal duct and tracing fluids from the nasal cavity.

In some embodiments there is provided a device for the treatment of a patient's canaliculus and nasolacrimal duct stenosis which comprises: a tube shaped and dimensioned to penetrate said canaliculus and duct; said tube being made of a substantially hard material, and having a proximal end, a blunted distal end, an axial lumen, a total length between approximately 4 and 50 centimeters and an outer diameter between 0.125 and 4.00 millimeters; a connector at said proximal end; said lumen having at least one orifice at said distal end.

In some embodiments said orifice comprises at least one radial outlet about 0.5 to 30 millimeters from said distal end, and said outlet has a diameter between about 0.025 and 2.5 millimeters. In some embodiments said material substantially is taken from a group consisting essentially of stainless steel, bronze, silver, aluminum, titanium, brass, and alloy thereof, Kevlar, Nitinol, polymide, Dacron, nylon, EPTFE and PVC; and said tube further comprises a slanted radial flange proximate to said connector. In some embodiments the device further comprises a flexible catheter having a distal end shaped and dimensioned to interlock with said connector, and a proximal end shaped and dimensioned to interlock with a syringe. In some embodiments said connector is shaped and dimensioned to interlock with a syringe. In some embodiments the device further comprises a stiffening rod diametrically sized to engage said lumen, and having a length at least equal said total length. In some embodiments said rod has an enlarged manipulable end section. In some embodiments the device further comprises a flexible sleeve having a proximal end, a distal end, an axial interior channel closed at said distal end and being dimensioned to allow said channel to be engaged by said tube, and a length shorter than said total length of said tube. In some embodiments said flexible sleeve has a radial hole proximate said distal end. In some embodiments said tube comprises a radial flange proximate to said connector, and wherein said sleeve comprises a first radial flange around said proximal end; said first radial flange being oriented at the same axial angle as the radial flange of said tube. In some embodiments said sleeve comprises a second radial flange distally proximate to said first radial flange. In some embodiments said sleeve further comprises a first sealing implement across said channel, proximate said proximal end. In some embodiments said sleeve further comprises an inflatable segment between said radial hole and said distal end. In some embodiments said sleeve further comprises a second sealing implement across said channel at a short proximal distance from said segment. In some embodiments said inflatable segment comprises said sleeve having a reduced wall thickness along said segment.

Some embodiments provide a method for probing the integrity of a patient's canaliculus and nasolacrimal duct which comprises the steps of: inserting the device of some embodiments through the patient's punctum and canaliculus down the lacrimal sac; tilting the device about 90 degrees into alignment with the nasolacrimal duct; pushing the device through the nasolacrimal duct down to the nasal cavity; injecting a tracing fluid through said connector; and recovering part of said fluid from the nasal cavity; whereby recovery of a trace of said fluid confirms that the device has penetrated all obstructions and entered the nasal cavity.

Some embodiments provide a method for intubating a patient's nasolacrimal duct which comprises the steps of: inserting the metallic tube and the sleeve of some embodiments through a patient's punctum, canaliculus into the lacrimal sac; tilting the sleeve and tube about 90 degrees into alignment with the patient's nasolacrimal duct; pushing the tube and sleeve through the nasolacrimal duct down to the nasal cavity; injecting a tracing fluid into the tube; verifying that the tube and sleeve have reached the nasal cavity by recovering traces of said fluid in said cavity; and withdrawing said tube from said sleeve.

Some embodiments provide a method for intubating a patient's nasolacrimal duct which comprises the steps of:

inserting the tube and the sleeve of some embodiments through a patient's punctum, canaliculus into the lacrimal sac; tilting the sleeve and tube about 90 degrees into alignment with the nasolacrimal duct; pushing the tube and sleeve through the nasolacrimal duct down to the nasal cavity; injecting a volume of fluid through said connector sufficient to inflate said inflatable segment; partially withdrawing said tube from said sleeve by a distance sufficient to bring said outlet between said proximal end of the sleeve and said sealing implement at a short proximal distance from the inflatable segment; injecting a tracing fluid into the tube; verifying that the tube and sleeve have reached the nasal cavity by recovering traces of said fluid in said cavity; and withdrawing said tube from said sleeve.

Some embodiments provide a method which further comprises inserting a stiffening rod diametrically sized to engage said lumen and having a length greater than said total length into said tube, prior to insertion of said tube into said sleeve. Some embodiments provide a method which further comprises inserting a stiffening rod diametrically sized to engage said lumen and having a length substantially greater than said total length into said tube prior to insertion of said tube into said sleeve. Some embodiments provide a method which further comprises connecting said tube to a suction device during said step of pushing. Some embodiments provide a method which further comprises connecting said tube to a suction device during said step of pushing. In some embodiments said step of recovering comprises connecting a suction device to said tube. In some embodiments said step of recovering comprises connecting a suction device to the proximal end of said tube. In some embodiments said step of pushing further comprises pushing said second flange inside said punctum and resting said first flange against the external rim of said punctum.

DESCRIPTION OF THE PREFERRED EMBODIMENTS

Figure 1:
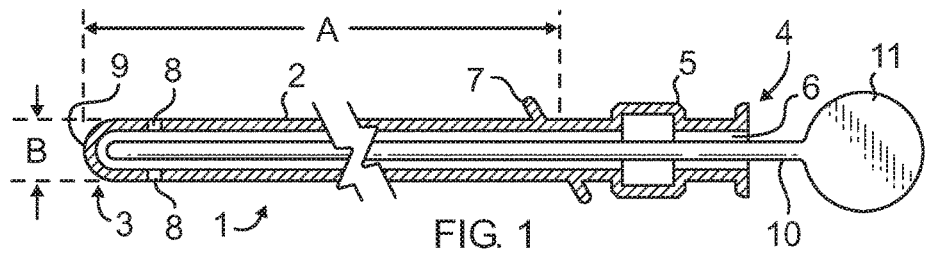
FIG. 1 is a cross-sectional view of a nasolacrimal probe according to the invention.

Referring now to the drawing, there is shown in FIG. 1 a cross-sectional view of nasolacrimal probe 1 specifically designed to probe obstructions in a patient's drainage system and nasolacrimal duct. The device comprises a tube 2 having a blunted distal end 3, an open proximal end 4 equipped with a luer-lock 5 or other type of connector, and axial lumen 6. An outwardly projecting radial flange 7 near the luer-lock is slanted at an angle from about 20 to 90 degrees, and can typically be 45 degrees to the axis of the probe. The probe can also be made without the flange. The device 1 is shaped and dimensioned for insertion through a patient's punctum and canaliculus, then through the lacrimal sac and into the nasolacrimal duct down to the nasal cavity down to the point where the flange 7 rests against the entry punctum. The device has a slight degree of flexibility resulting from the choice of material and its dimensions. The tube 2 and connector 5 are preferably made of a metal such as stainless steel, titanium, silver, aluminum, bronze, brass or any alloy of these metals, or of synthetic materials such as Kevlar, Nitinol, polymide, Dacron, nylon, EPTFE or PVC. The total insertable length A is preferably 10 centimeters, but may fall between approximately 5 and 50 centimeters. The outer diameter B of the tube, is preferably 0.64 millimeters, but may range from approximately 0.10 to 3.75 millimeters.

One or a pair of diametrically opposite radial orifices or outlets 8 are located 0.5 to 30 millimeters approximately from the distal end 3. The diameter of each outlet is preferably 0.025 millimeters, but can reach 2.5 millimeters in large models. The distal end is blunted by a rounded or conical tip 9. Alternately, a single axial orifice with a rounded lip to prevent abrasion may be provided at the distal end of the tube with a diameter of, preferably, 0.25 millimeters, but could fall anywhere between 0.025 and 2.5 millimeters. Although the tube is made of a rigid or semi-rigid material its length and the relative thinness of its wall may render it quite flexible and easily bendable. To avoid damaging the tube and generally increase its rigidity, a stiffening rod 10 diametrically sized to engage the lumen 6 of the tube is provided. The rod has a length slightly in excess of the total length A of the tube, and is made of the same type of material. A manipulable flattened or otherwise enlarged section 10a at the proximal end of the rod facilitates its handling.

Figure 7:
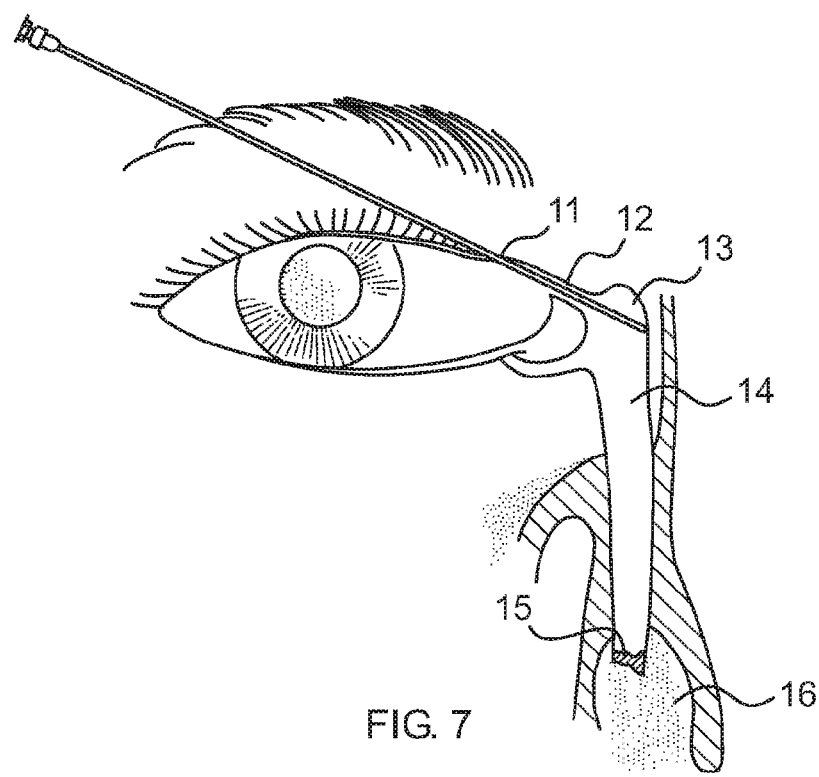
FIG. 7 illustrates the first positioning of the probe.
Figure 8:
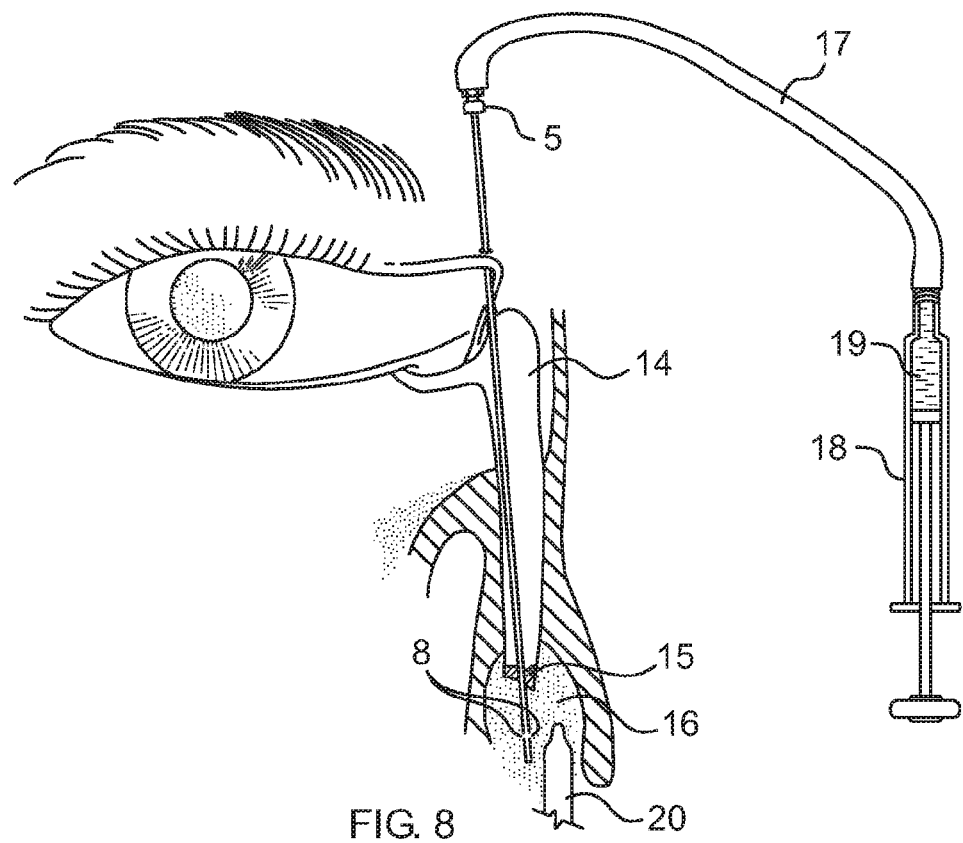
FIG. 8 illustrates the final position of the probe.

Probing of the nasolacrimal duct with the device 1 begins with inserting the tube through a patient's punctum 11 and canaliculus 12 down to the lacrimal sac 13, as shown in FIG. 7. A barrier is felt when the probe encounters the medial lacrimal sac wall and lacrimal fossa. At that point, the probe is then retracted about 0.5 millimeters and is tilted about 90 degrees into alignment with the nasolacrimal duct 14 as illustrated in FIG. 8. The probe is pushed down the nasolacrimal duct through any obstruction 15 and into the nasal cavity 16. A flexible conduit 17 is connected at one end to the connector 5 and at the other end to a syringe 18 loaded with fluorescein or methylene blue stained fluid 19 or any other colored liquid or gas tracer. Alternately the syringe may be applied directly to the connector 5. The fluid is injected to irrigate through the probe into the nose. The fluid flows out of the outlets 8 into the nasal cavity. Traces of the fluid can be recovered in the nose with a suction catheter 20. A lack of fluid recovery in the nose indicate that the probe has not penetrated all obstructions and reached the nose. The surgeon can then push with greater force or pull the probe back slightly and drive it into the nasal cavity at a slightly different angle. Detection of the tracer fluid into the nose is a positive indication that all obstructions have been cleared, and no divergent passage through tissues surrounding the nasolacrimal duct has been opened by the probe.

It should be noted that the surgeon does not have to perform the difficult and sometime impossible task of touching the tip of the probe in the nose with another metal instrument to confirm that the probe has duly entered the nasal cavity. Furthermore, the irrigation does not have to be performed as a second procedure after a solid probe of the prior art has been withdrawn from the lacrimal system. No second probing needs to be done if the irrigation is not successful.

The stiffening rod 10 must be withdrawn before the flexible tube or syringe is connected to the probe. Preferably, the rod is used when the probe encounters an obstacle and cannot readily and safely be pushed through it.

Figure 2:
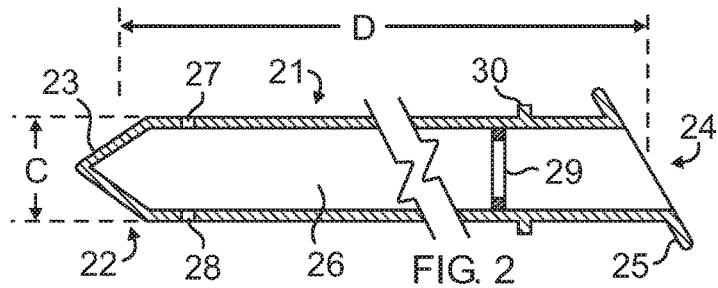
FIG. 2 is a cross-sectional view of an intubation sleeve.
Figure 3:
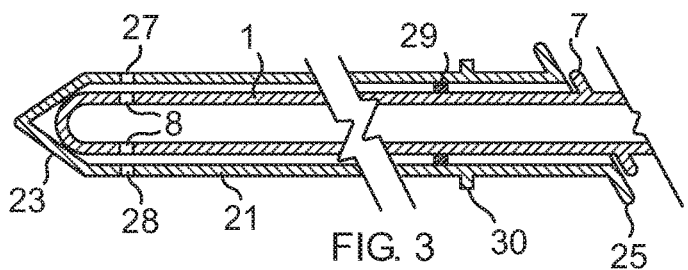
FIG. 3 is a partial cross-sectional view of a combination of the aforesaid probe and sleeve.

Referring now to FIG. 2, there is shown an intubation sleeve 21 shaped and dimensioned to be used in connection with the above-described probe 2. The outer diameter of the sleeve is preferably 1.125 millimeters, but could fall between 0.25 and 4.0 millimeters. The sleeve is flexible and preferably made of silicone, polypropylene or other medically approved synthetic material. The distal end of the sleeve 22 is preferably closed by a conical tip 23 or a rounded one substantially similar to the tip 9 of the probe. The proximal end 24 of the sleeve is open and is surrounded by a first outwardly projecting radial flange 25 that is oriented at an angle between 20 to 90 degrees and preferably approximately 45 degrees with the axis of the sleeve like the flange 7 of the probe. The internal channel 26 of the sleeve is dimensioned to be loosely engaged by the probe 1 as shown in FIG. 3 so that a fluid injected into the probe can readily exit the radial holes 8 or the axial orifice at the distal end of the probe and flow freely into the sleeve. The insertable length D of the sleeve is about 3 millimeters shorter than the insertable length A of the probe.

A hole 27, or alternatively two diametrically opposite radial holes 27, 28, bored through the sleeve at approximately the same distance from the tip 23 as the distance between the outlets 8 of the probe are from its tip 3, let tracing or irrigating fluid injected into the probe escape from the sleeve into the nasal cavity. An O-ring, self-sealing diaphragm 29, or other type of sealing implement located between 0 and 100 millimeters and preferably about 3 millimeters from the proximal end 24 of the sleeve can be penetrated by the probe and maintain a hermetic barrier that will prevent any fluid in the channel 26 from leaking through the proximal end 24 of the sleeve. A second radial flange 30 distally proximate to the first flange 25 is designed to lie just inside the punctum to keep the first flange resting against the edge of the punctum. The second flange can have an oval shape, and have a maximum exterior diameter between 0.3 and 6 millimeters, preferably 2.5 millimeters, and is preferably orthogonal to the axis of the sleeve.

Intubation of the nasolacrimal duct is performed by first inserting the probe 1, and optionally its stiffening rod 10, into the sleeve 21 until the tip of the probe touches the closed distal end of the sleeve as shown in FIG. 3. The combined probe and sleeve are then threaded through a patient's punctum, canaliculus, lacrimal sac, nasolacrimal duct all the way down to the nose in the same manner as described above and illustrated in FIGS. 7 and 8 in connection with the probe, until the second flange 30 is set into the patient's punctum and the first flange 25 rests against the external rim of the punctum.

The surgeon may encounter resistance when pushing the second radial flange 30 of the sleeve through the punctum into the proximal canaliculus if the punctum is somewhat small in diameter. The distal end of the probe will exert pressure upon the very distal end of the sleeve if the surgeon applies a large amount of force on the probe while attempting to push the second radial flange 30 through the punctum. However, puncture of the distal end of the sleeve is prevented by the slanted flange 7 of the probe coming into contact with the slanted flange 25 of the sleeve. This stops further penetration of the probe into the sleeve, while allowing the surgeon to apply pressure on the probe and sleeve assembly in order to push the second flange 30 of the sleeve through the punctum.

Figure 6:
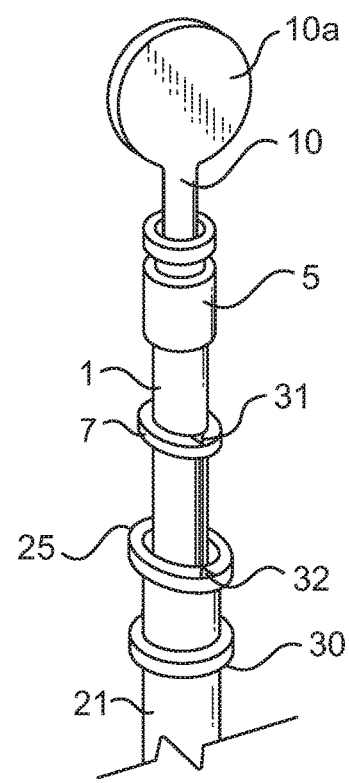
FIG. 6 is a perspective view of the proximal end of the probe and sleeve combination.

If the internal diameter of the sleeve closely matches the external diameter of the probe, irrigation may be facilitated by aligning the outlets with the holes, as shown in FIG. 6. A mark 31 along the external wall of the probe that is aligned with one of the outlets 7, 8 is brought to match an indicium 32 on the flange 25 of the sleeve 21 that is aligned with one of the holes 27, 28.

After the presence of the sleeve and probe in the nasal cavity has been verified by the collection of some of tracing liquid in the nasal cavity, the probe is withdrawn leaving the sleeve in place.

Figure 4:
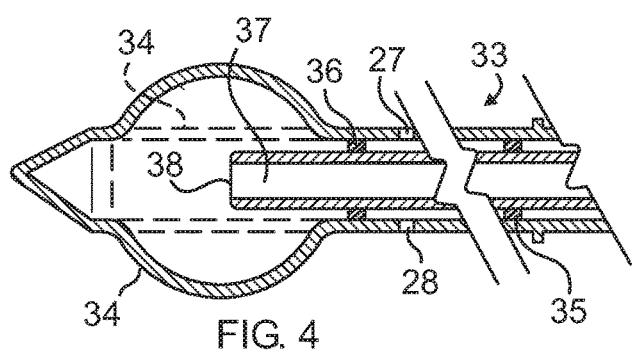
FIG. 4 is a partial cross-sectional view of an alternate embodiment of the sleeve in the inflated position.
Figure 5:
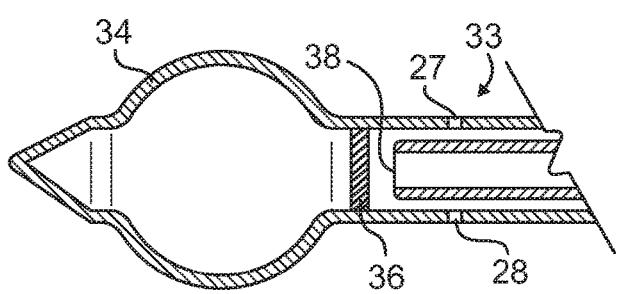
FIG. 5 is a cross-sectional view of the alternate embodiment of the sleeve in the irrigating position.
Figure 9:
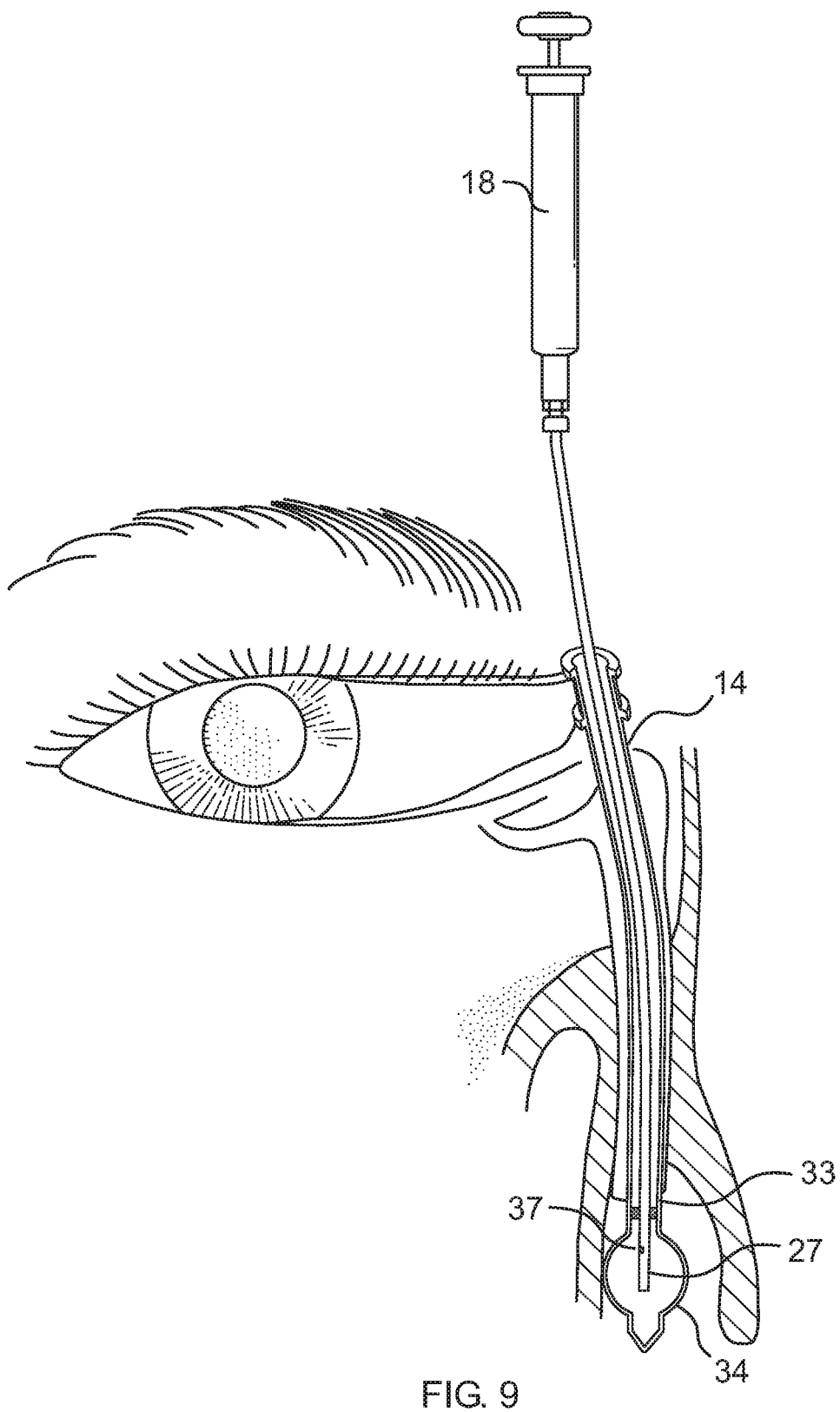
FIG. 9 illustrate intubation with sleeve having an inflatable end segment.

In an alternate version 33 of the sleeve illustrated in FIGS. 4 and 5, an inflatable segment 34 is formed near the distal end of the sleeve. The inflatable segment is preferable implemented using a resiliently expandable material, or by a reduction in the thickness of the sleeve wall slightly distally from the radial holes 27 and 28 in order to create a resiliently expandable balloon under internal pressure. Alternatively a segment made of easily expanded material can be attached to the distal end of a non-expandable sleeve. The entire sleeve can also be made of easily expanded sheet material. A first O-ring, self-sealing diaphragm 35 or other self-sealing implements may optionally be positioned between the proximal end of the sleeve and the radial holes, preferably at a short distance from the proximal end of the sleeve. A second self-sealing implement 36 is positioned between the radial holes 27, 28 and the inflatable segment 34. A fluid can be injected through a probe 37 having an axial orifice 38 or, alternatively, at least one radial orifice at its distant end, after the probe has been used to push the sleeve into position through the patient's punctum, canaliculus, lacrimal sac and nasolacrimal duct into the nasal cavity with the open tip of the probe resting in or just past the inflatable segment. The injection of the fluid causes the inflatable segment to bellow out and positively lock the sleeve in position as illustrated in FIG. 9. The probe is then withdrawn to a distance sufficient to place the orifice 38 between the first 35 and the second 36 self sealing implements as shown in FIG. 5. Additional injection of tinted fluid will cause the fluid to escape into the nasal cavity through the axial orifice 38 into the sleeve. The second self sealing implement 36 prevents fluid from leaking out of the inflated area 34, thus maintaining the inflation. The first self sealing implement 35 prevents leakage of the fluid out of the proximal end of the sleeve, causing the fluid to exit through the radial holes 27, 28. Once the correct positioning of the sleeve has been verified through the collection of tracing fluid in the nasal cavity, the probe can be withdrawn while the sleeve distal segment remains inflated keeping the sleeve safely in place. In both cases, the sleeve can be later removed by grasping the flange 25 and pulling the sleeve out of the lacrimal system. Prior to removal, the end segment 34 can be deflated by pushing the probe through the second self sealing implement 36, and letting the fluid escape into the nasal cavity or suctioning it through the probe as explained below. Otherwise, the fluid will be allowed to slowly leak out of the sleeve on its own, whereupon the sleeve can be removed days, weeks or even months later.

Figure 10:
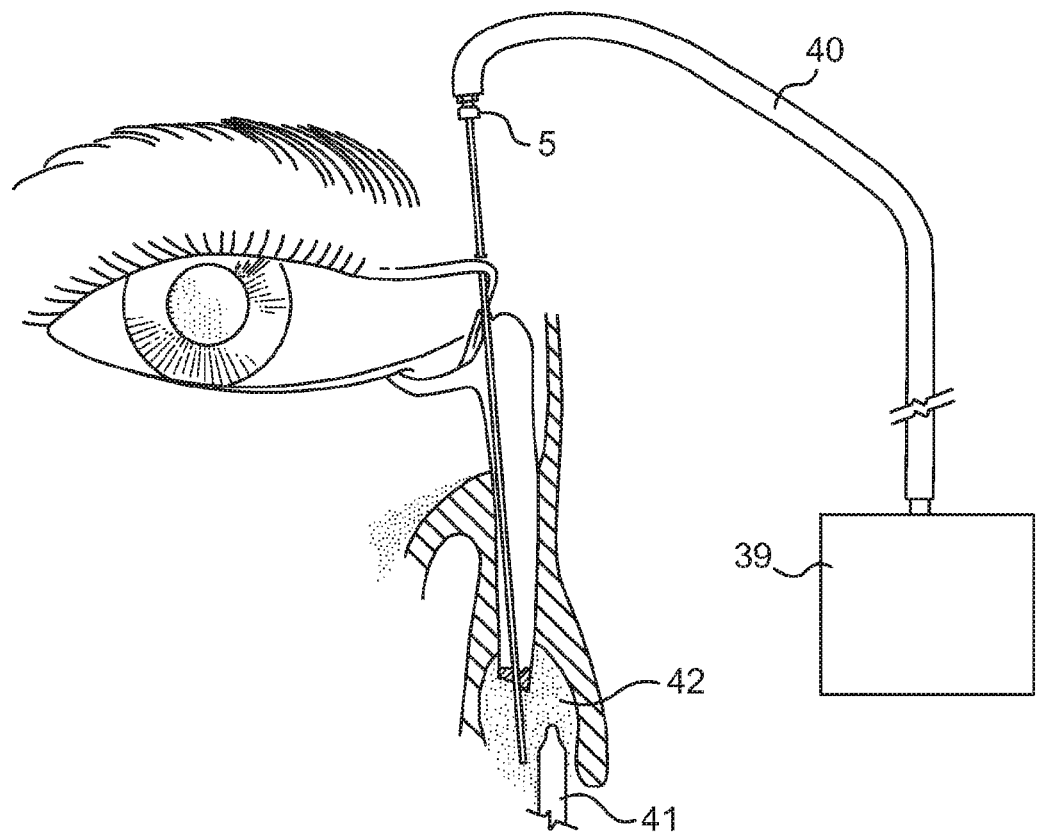
FIG. 10 illustrates suction through the probe.

Each of the probes 1, 37 can be used for suctioning blood from the lacrimal system or nasal cavity caused by the probing or intubating process, as well as for suctioning the tracer fluid from the nasal cavity as illustrated in FIG. 10.

At the end of the probing or intubation procedure or after having been pushed through the lacrimal system as described above, the probe with or without either of the sleeves 21, 33 is connected to a suction device 39 by way of a catheter 40. Suction is then performed to either retrieve the tracer fluid out of the nasal cavity or to remove blood caused by abrasion during the procedure. The suction device may also be connected and activated during the insertion process of the probe or probe-and-sleeve combination through the nasolacrimal system in order to suction any obstructive tissue or blood. After installation of the probe or probe-and-sleeve combination, a tracer fluid may be injected with a syringe or eye dropper 41 through the nares 42. The fluid is then retrieved through the probe connected to the suction device to confirm proper placement of the sleeve or that the probe has reached the nasal cavity.

It can thus be seen that the tubular probe of the invention is a very versatile instrument that can be used not only for probing the nasolacrimal ducts, but also to perform intubation, irrigation and even suction of obstructive material.

While the preferred embodiments of the invention have been described, modifications can be made and other embodiments may be devised without departing from the spirit of the invention and the scope of the appended claims.

What is claimed is:

1. A device for the treatment of nasolacrimal obstructions which comprises:
    a tube made of a substantially hard semi-rigid material, and having a proximal end, a blunted distal end, an axial lumen, a total length between approximately 4 and 50 centimeters and an outer diameter between 0.125 and 4.00 millimeters;
    a connector at said proximal end;
    said lumen having at least one orifice at said distal end; and,
    a flexible sleeve having a proximal end, a distal end, an axial interior channel closed at said distal end and being dimensioned to allow said channel to be engaged by said tube leaving a radial gap between said tube and said sleeve, allowing fluid to pass through said gap;
    said sleeve having a length shorter than said total length of said tube;
    wherein said sleeve further comprises:
        a first seal against said tube near said distal end; and,
        an inflatable segment between said proximal end and said distal end.

2. The device of claim 1 wherein said orifice comprises at least one radial outlet about 0.5 to 30 millimeters from said distal end, and said outlet has a diameter between about 0.025 and 2.5 millimeters.

3. The device of claim 1 wherein said material substantially is taken from a group consisting essentially of stainless steel, bronze, silver, aluminum, titanium, brass, and alloy thereof, Kevlar, Nitinol, polyimide, Dacron, nylon, EPTFE and PVC; and said tube further comprises a slanted radial flange proximate to said connector.

4. The device of claim 1, wherein said connector is shaped and dimensioned to interlock with a pressurized fluid source.

5. The device of claim 1, which further comprises a stiffening rod diametrically sized to engage said lumen.

6. The device of claim 5, wherein said rod has a length at least equal to said total length.

7. The device of claim 6, wherein said rod has an enlarged manipulable end section.

8. The device of claim 1, wherein said flexible sleeve has a radial hole proximate said distal end.

9. The device of claim 1, wherein said tube comprises a radial flange proximate to said connector, and wherein said sleeve comprises a first radial flange around said proximal end; said first radial flange being oriented at the same axial angle as the radial flange of said tube.

10. The device of claim 9, wherein said sleeve comprises a second radial flange distally proximate to said first radial flange.

11. The device of claim 1, wherein said inflatable segment comprises said sleeve having a reduced wall thickness along said segment.

12. A method for intubating a patient's nasolacrimal duct which comprises the steps of:
    inserting the tube and the sleeve of claim 1 through a patient's punctum, into the lacrimal sac;
    tilting the sleeve and tube about 90 degrees into alignment with the patient's nasolacrimal duct;
    pushing the tube and sleeve through the nasolacrimal duct down to the nasal cavity;
    injecting a tracing fluid into the tube;
    verifying that the tube and sleeve have reached the nasal cavity by recovering traces of said fluid in said cavity;
    inflating said inflatable segment through said gap; and withdrawing said tube and said sleeve.

13. The method of claim 12, which further comprises inserting a stiffening rod diametrically sized to engage said lumen.

14. The method of claim 12, which further comprises connecting said tube to a suction device during said step of pushing.

15. The method of claim 12, wherein said step of recovering comprises connecting a suction device to said tube.

* * * * *